United States Patent
Cheng et al.

(10) Patent No.: US 6,540,681 B1
(45) Date of Patent: Apr. 1, 2003

(54) EXTENDED VIEW ULTRASOUND IMAGING SYSTEM

(75) Inventors: Xiangyong Cheng, Cupertino, CA (US); Shengtz Lin, Cupertino, CA (US)

(73) Assignee: U-Systems, Inc., Los Altos, CA (US)

( * ) Notice: Subject to any disclaimer, the term of this patent is extended or adjusted under 35 U.S.C. 154(b) by 5 days.

(21) Appl. No.: 09/721,645

(22) Filed: Nov. 24, 2000

(51) Int. Cl.$^7$ .................................................. A61B 8/00
(52) U.S. Cl. ...................................... 600/443; 345/153
(58) Field of Search ......................... 600/443; 128/916; 345/589; 382/162

(56) References Cited

U.S. PATENT DOCUMENTS

| | | | |
|---|---|---|---|
| 4,887,306 A | | 12/1989 | Hwang et al. |
| 5,353,354 A | | 10/1994 | Keller et al. |
| 5,566,674 A | | 10/1996 | Weng |
| 5,632,277 A | | 5/1997 | Chapman et al. |
| 5,782,766 A | * | 7/1998 | Weng et al. ................ 128/916 |
| 5,831,604 A | | 11/1998 | Gerber |
| 6,102,865 A | | 8/2000 | Hossack et al. |
| 6,104,473 A | | 8/2000 | Konagaya |
| 6,132,376 A | * | 10/2000 | Hossack et al. ............ 600/443 |
| 6,144,365 A | * | 11/2000 | Young et al. ............... 345/589 |
| 6,159,152 A | * | 12/2000 | Sumanaweera et al. ..... 600/443 |

\* cited by examiner

*Primary Examiner*—Marvin M. Lateef
*Assistant Examiner*—Ruby Jain
(74) *Attorney, Agent, or Firm*—Cooper & Dunham LLP (57) ABSTRACT

An extended view ultrasound imaging system in which a position sensor is used to detect the location and orientation of a ultrasound transducer for each scan frame as the ultrasound transducer is swept across the surface of a target. The contents of the successive scan frames, together with their location and orientation information, are processed to generate an extended view ultrasound image of the target region. An output array representing the extended view image is first initialized, and then successively updated as each scan frame is received. In a preferred embodiment, an alpha-blending algorithm is used to combine the information in the current scan frame with previous output array values to generate the current output array values. Because the content of the successive image frames is not relied upon to piece them together, system processing requirements are substantially reduced and the output image is robust against increased transducer speed, bumps in the transducer path, and departures of the transducer from a common plane. In an additional preferred embodiment, the alpha-blending weighting factor can be user-adjustable and/or can be dynamically adjusted on a per-location basis based on acoustic reflectivity, edge motion, or other factors. Also in an additional preferred embodiment, the amount of departure from a common plane during the movement of the transducer across the target can be displayed to the user for assistance in interpreting the extended view image.

23 Claims, 6 Drawing Sheets

EXTENDED VIEW ULTRASOUND IMAGING SYSTEM

FIELD

This patent specification relates to the field of ultrasound information processing systems. In particular, it relates to a method and system for generating extended view ultrasound images.

BACKGROUND

Ultrasound imaging systems have become increasingly popular for use in medical diagnosis because they are non-invasive, easy to use, and do not subject patients to the dangers of electromagnetic radiation. Instead of electromagnetic radiation, an ultrasound imaging system transmits sound waves of very high frequency (e.g., 2 MHz to 10 MHz) into the patient and processes echoes reflected from structures in the patient's body to derive and display information relating to these structures.

Conventional ultrasound probes often have a limited field of view compared to the target being imaged, and it is often difficult for a human observer to visualize the whole target from conventional displays of this limited field of view. Responsive to this problem, ultrasound imaging systems have been proposed that create extended view or panoramic images that are more useful in visualizing the target region as a whole. The extended view images are generated by piecing together sequential images taken as the probe is moved in a common plane across the target surface.

One such extended view ultrasound imaging system is discussed in U.S. Pat. No. 5,782,766, which is incorporated by reference herein. According to the '766 approach, sequential image frames are pieced together by correlating information in the sequential frames to determine a transducer position and orientation associated with each frame, and then using the computed transducer positions and orientations to piece together the sequential frames into an extended view image. The correlation step includes the steps of (i) using a motion detection routine on information in successive images to compute an initial estimation of local motion vectors, (ii) using a fuzzy logic technique to combine the initial estimation with two measurement parameters to derive a final estimation of the local motion vectors, and (iii) applying a least-squares process to the final local motion vectors to estimate global image motion.

The system described in the '766 patent has several disadvantages due to its use of a correlation algorithm to determine transducer position and orientation. First, the '766 approach can introduce substantial computational complexity into the imaging process, resulting in reduced system speed, increased system size and complexity, and increased system cost. Second, because of its dependence on inter-frame similarities, the '766 approach limits the speed of movement of the transducer across the target, and even proposes a "speedometer" for informing the user when the movement is too fast. Third, the '766 approach is intolerant to tissue motion in the target region, such as the motion of a beating heart, because of its dependence on inter-frame similarities. For similar reasons, the '766 approach is also intolerant to bumps in the trajectory of the transducer, such as those cause by skin surface irregularities or shakiness in the hand of the user. Moreover, the '766 approach depends on the user to maintain the transducer's position and orientation in a common plane as it is moved across the target. If the transducer deviates from that common plane, the correlation algorithm may yield inaccurate results or may completely break down. Even if the correlation algorithm does not break down, the ultimate display may be misleading to the viewer as there may be no way for the '766 algorithm to detect deviations from the common plane.

Finally, it is believed that the conceptual circularity of the '766 algorithm—in which relative image content is used to compute the very parameters that are used to "line up" that relative image content—introduces limitations on the output image quality, especially when the user moves the transducer more quickly across the target or guides the transducer away from the common plane. In particular, it is believed that the transducer's estimated position and orientation has an image-dependent degree of error that can frustrate the increases in output quality that would traditionally be enjoyed by image compounding. Furthermore, this error increases as the user increases the speed of the transducer across the target surface or guides the transducer away from the common plane.

Accordingly, it would be desirable to provide an extended view ultrasound imaging system that has reduced computational requirements, resulting in increased system speed and reduced system size, cost, and complexity.

It would be further desirable to provide an extended view ultrasound imaging system that produces an output image that is robust against increased transducer speed as it is moved across a target surface.

It would be even further desirable to provide an extended view ultrasound imaging system that is tolerant of tissue motion in the target region and tolerant of bumps in the trajectory of the transducer.

It would be still further desirable to provide an extended view ultrasound imaging system that is robust against deviations of the transducer from a common plane as it is moved across a target surface.

It would be even further desirable to provide an extended view ultrasound imaging system that is capable of notifying the user when the transducer has substantially deviated from the common plane, and/or capable of informing the user of the amount of deviation from the common plane.

It would be still further desirable to provide an extended view ultrasound imaging system that constructs the extended view image using a stable algorithm that decreases speckle and increases signal-to-noise ratio.

SUMMARY

In accordance with a preferred embodiment, a system for generating extended view ultrasound images is provided in which an ultrasound transducer generates a sequence of scan frames as it is swept across the surface of a target, wherein a position sensor is used to detect the location and orientation of the transducer for each scan frame. The contents of the successive scan frames, together with their location and orientation information, are then processed to generate an extended view ultrasound image of the target region. An output array representing the extended view image is first initialized, and then successively updated as each scan frame is received. In accordance with a preferred embodiment, an alpha-blending algorithm is used to combine the information in the current scan frame with the previous output array values to generate the current output array values.

Advantageously, because the content of the successive image frames is not relied upon to piece them together, the system's processing requirements are substantially reduced and the output image is robust against increased transducer speed, bumps in the transducer path, and departures of the transducer from a common plane. Moreover, it has been found that the use of an alpha blending algorithm can provide a high quality image with reduced speckle, increased signal to noise ratio, and enhanced contrast resolution even if the spatial precision of the position sensor is less than the spatial resolution of the scan frames themselves.

In accordance with a preferred embodiment, the weighting factor $\alpha$ is a predetermined value that is used to weight the current scan frame value, while the quantity $(1-\alpha)$ is used to weight the previous output array value, with the current value of the output array being set equal to the sum of the results. Alternatively, the value of $\alpha$ may be user-adjustable, whereby the user can adjust it closer to 1.0 for increased temporal resolution, e.g., during an extended view scan of a beating heart, or closer to 0.0 for stationary tissue to achieve further decreased speckle and increased signal to noise performance. In alternative preferred embodiments, the weighting factor may be automatically and dynamically adjusted on a per-pixel basis responsive to any of a variety of factors, including location reflectivity, edge motion, or the presence of a systolic cycle versus a diastolic cycle in the patient being imaged.

In accordance with another preferred embodiment, information related to departure of the scan frames from a common plane is computed and displayed to the user. In contrast to prior art systems in which the extended view algorithm breaks down upon substantial departure from a common plane, a system in accordance with the preferred embodiments is not only tolerant to such departure, but can compute the amount of departure and display it to the user for assistance in interpreting the extended view image. Thus, instead of a common plane trajectory, the user may alter the trajectory of the transducer such that the scan planes form a ribbon-like path through the target. The amount of deviation from the common plane may be displayed to the user in a variety of ways, such as by coloring the extended view image on a per location basis to reflect linear departure distances, or by providing a separate graphical display next to the extended view image to reflect the angular departure of the transducer on a per scan line basis.

DETAILED DESCRIPTION

Figure 1:
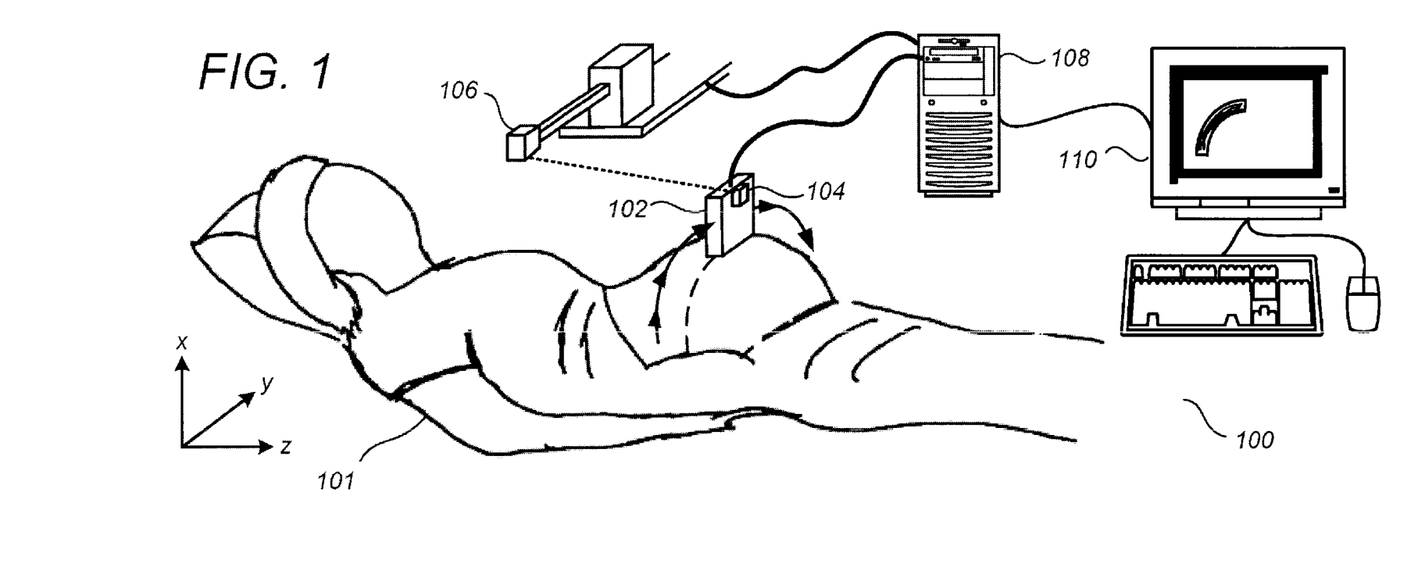
FIG. 1 shows an extended view ultrasound imaging system in accordance with a preferred embodiment.

FIG. 1 shows an extended view ultrasound imaging system 100 in accordance with a preferred embodiment, as an extended view scan of a patient 101 is performed. Extended view ultrasound imaging system 100 comprises an ultrasound transducer 102, a position sensor scanhead portion 104, a position sensor stationary portion 106, an ultrasound processing unit 108, and a display device 110. Ultrasound transducer 102 may be any of a variety of commercially available ultrasound transducers comprising a substantially linear array of transducer elements that may be swept across a target surface as shown in FIG. 1.

Position sensor scanhead portion 104 and position sensor stationary portion 106 may be any of a variety of off-the-shelf ultrasound position sensing devices, such as the mini-BIRD 800™ position sensing system available from Ascension Technology Corp. of Burlington, Vt. Although the position sensing system used in FIG. 1 is a two-part system comprising a scanhead portion and a stationary portion, the scope of the preferred embodiments is not so limited. For example, provided they are of sufficient resolution, one-piece accelerometer-based position sensors may be used. Importantly, it has been found that the extended view imaging algorithms described infra produce high-quality results even where the spatial resolution of the position sensing device is not as great as the spatial resolution of the individual scan frames being processed. For example, it has been found that a system according to the preferred embodiments may use a miniBIRD 800™ position sensing system, which has a spatial resolution of about 0.5 mm, in conjunction with an ultrasound system whose scan frames have a spatial resolution of 0.1 mm, and can still yield high-quality extended view images.

Ultrasound processing unit 108 may be special-purpose hardware adapted to carry out the algorithms described infra, or may be a general-purpose ultrasound processing system capable of running a computer program for carrying out these algorithms. Given the present disclosure, one skilled in the art will be readily able to deploy special-purpose hardware or program a general-purpose ultrasound system to achieve the functionalities of ultrasound processing unit 108 described infra in accordance with the preferred embodiments.

Display device 110 may be any of a variety of display devices capable of forming a viewable image based on data provided by ultrasound processing unit 108. Indicated on the display device 110 of FIG. 1 is a real-time embodiment, wherein an extended view ultrasound image is computed and displayed in real-time as the ultrasound transducer 102 is swept across the target surface. However, the scope of the preferred embodiments is not so limited. The extended view image computed by ultrasound processing unit 108 may instead be stored for later viewing or subsequent processing by downstream ultrasound devices.

Figure 2:
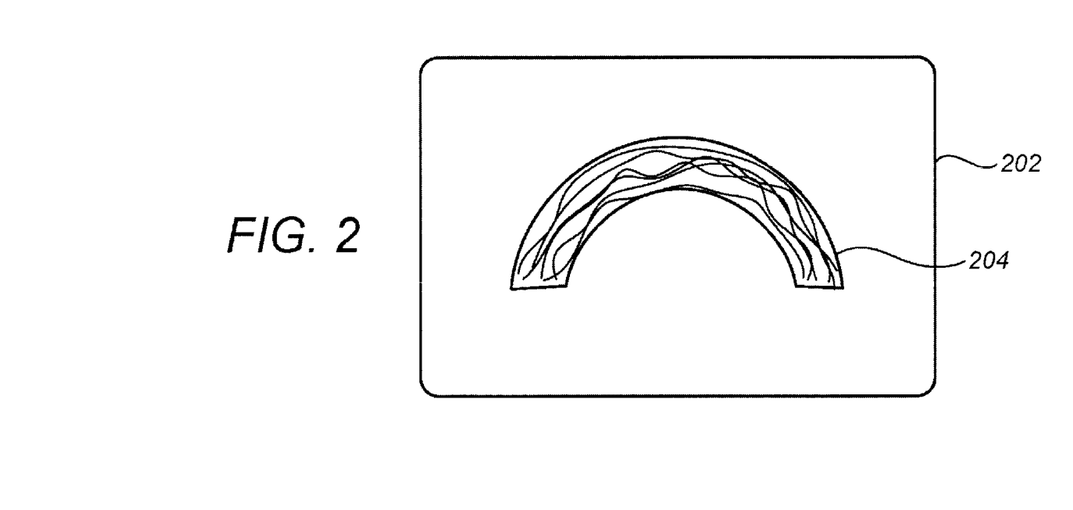
FIG. 2 shows an example of an extended view image created by the extended view ultrasound imaging system of FIG. 1.

FIG. 2 shows a closer view of a display device 202 displaying an extended view ultrasound image 204 computed in accordance with the preferred embodiments. The extended view ultrasound image 204 of FIG. 2 is arc-shaped in accordance with the trajectory of the ultrasound transducer 102 in FIG. 1. In general, however, the ultimate shape of the extended view ultrasound image will depend on the trajectory of the ultrasound transducer 102. For example, where the transducer is swept directly down the side of a patient's arm, the shape will be rectangular. If display space becomes exhausted during a real-time scan, the display device 202 will automatically scroll to follow the most recent scan frames received.

Figure 3:
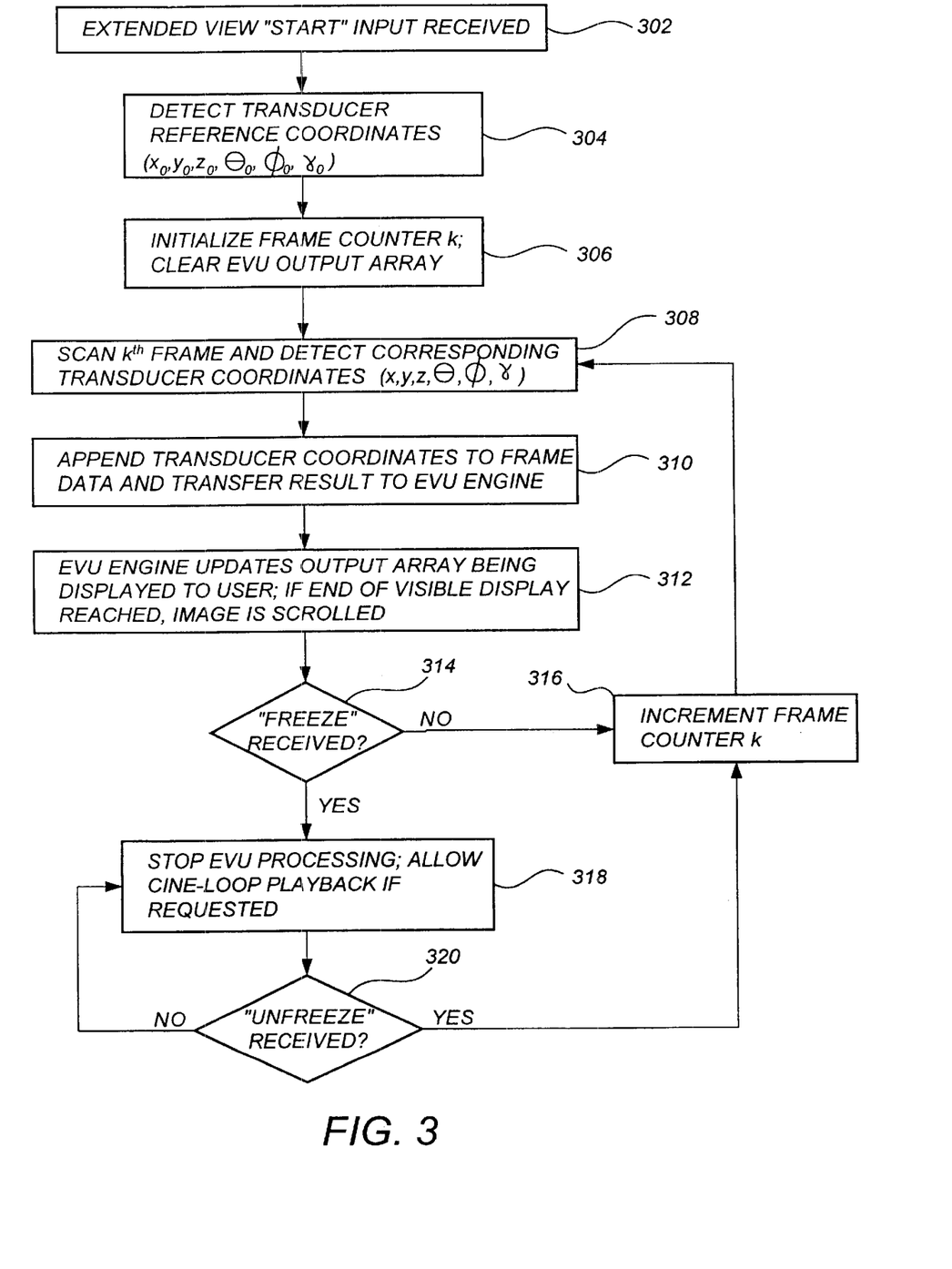
FIG. 3 shows overall steps for creating an extended view ultrasound image in accordance with a preferred embodiment.

FIG. 3 shows overall steps for creating an extended view ultrasound image in accordance with a preferred embodiment. At step 302, an extended view start input is received from the user, e.g., through the squeezing of a trigger on the ultrasound transducer 102 or the pressing of a start button near the display device 110. At step 304, transducer reference coordinates $(x_0, y_0, z_0, \theta_0, \phi_0, \gamma_0)$ are detected by the position sensing elements 104 and 106 for subsequent use in computing location and orientation information for each scan frame as the ultrasound transducer 102 is swept across the surface of the target. It is to be appreciated that position sensor scanhead portion 104 is offset by a constant amount from the actual position of the array elements of ultrasound transducer 102, and so a constant offset from the sensor readings is applied before using them to establish the reference coordinates. At step 306, a frame counter "k" and an extended view ultrasound output array are initialized at ultrasound processing unit 108 in preparation for processing successive scan frames denoted by the counter variable k.

The user then sweeps the ultrasound transducer 102 across the target surface. Advantageously, for most practical purposes, the user is not limited to a maximum linear speed of the ultrasound transducer 102 across the target surface, because the content of successive scan frames is not relied upon to piece them together. Rather, the images are pieced together based on the location of ultrasound transducer 102 as detected by position sensing elements 104 and 106, and therefore the extended view output image is robust against increased transducer speed, bumps in the transducer path, and departures of the transducer from a common plane. Indeed, using a typical frame rate of 20 frames per second and an effective scan frame aperture of 5 cm, a system according to the preferred embodiments would still generate an unbroken extended view image at a transducer speed of 100 cm per second, which is well beyond the practical speed at which any user would want to move the transducer in medical applications. It should be noted, however, that the advantages of image compounding (including reduced speckle, increased signal-to-noise ratio, and enhanced contrast resolution) are enhanced as the transducer speed is decreased. If a more exemplary transducer speed of 5 cm/s is used in the above system, each location in the extended view image (except for locations near the start and end points) will be based on readings from 400 separate scan frames at that location. Although the system of the preferred embodiments is robust against bumps in the transducer path, it is nevertheless advisable in medical applications to use a lubricated gel bag between the transducer head and the patient's skin to reduce bumps and discontinuities.

At step 308, the $k^{th}$ scan frame is generated and corresponding transducer coordinates $(x, y, z, \theta, \phi, \gamma)$ are detected. At step 310, the transducer coordinates $(x, y, z, \theta, \phi, \gamma)$ are appended to the scan frame data, which is then transferred to ultrasound processing unit 108. At step 312, ultrasound processing unit 108 operates on the received data using an algorithm described infra, generating an updated output array for real-time display at output device 110 and/or for subsequent storage and non-real-time viewing or processing. If the end of the visible display is reached, the image on the output display 110 is scrolled.

At step 314, it is determined whether a user freeze command was received, this command being effectuated, for example, by releasing a trigger on the ultrasound transducer 102 or pressing a freeze button near the display device 110. If a freeze command was not received, then the frame counter k is incremented at step 316 and the process continues for the next scan frame at step 308. If a freeze command was received, then at step 318 extended view processing is suspended. At this time, using methods known in the art, the user is permitted to request and view a cine-loop playback of the generation of the output array and/or of the components scan frames. At step 320, it is determined whether an unfreeze command has been received, e.g., by the user again pressing a trigger on the ultrasound transducer 102. If not, the suspension of extended view processing continues at step 318. If so, the frame counter k is incremented at step 316 and the algorithm continues at step 308. Advantageously, because the system is robust against trajectory variances of the ultrasound transducer 102, processing remains stable and reliable even if the user moves the ultrasound transducer 102 during the freeze period.

Figure 4:
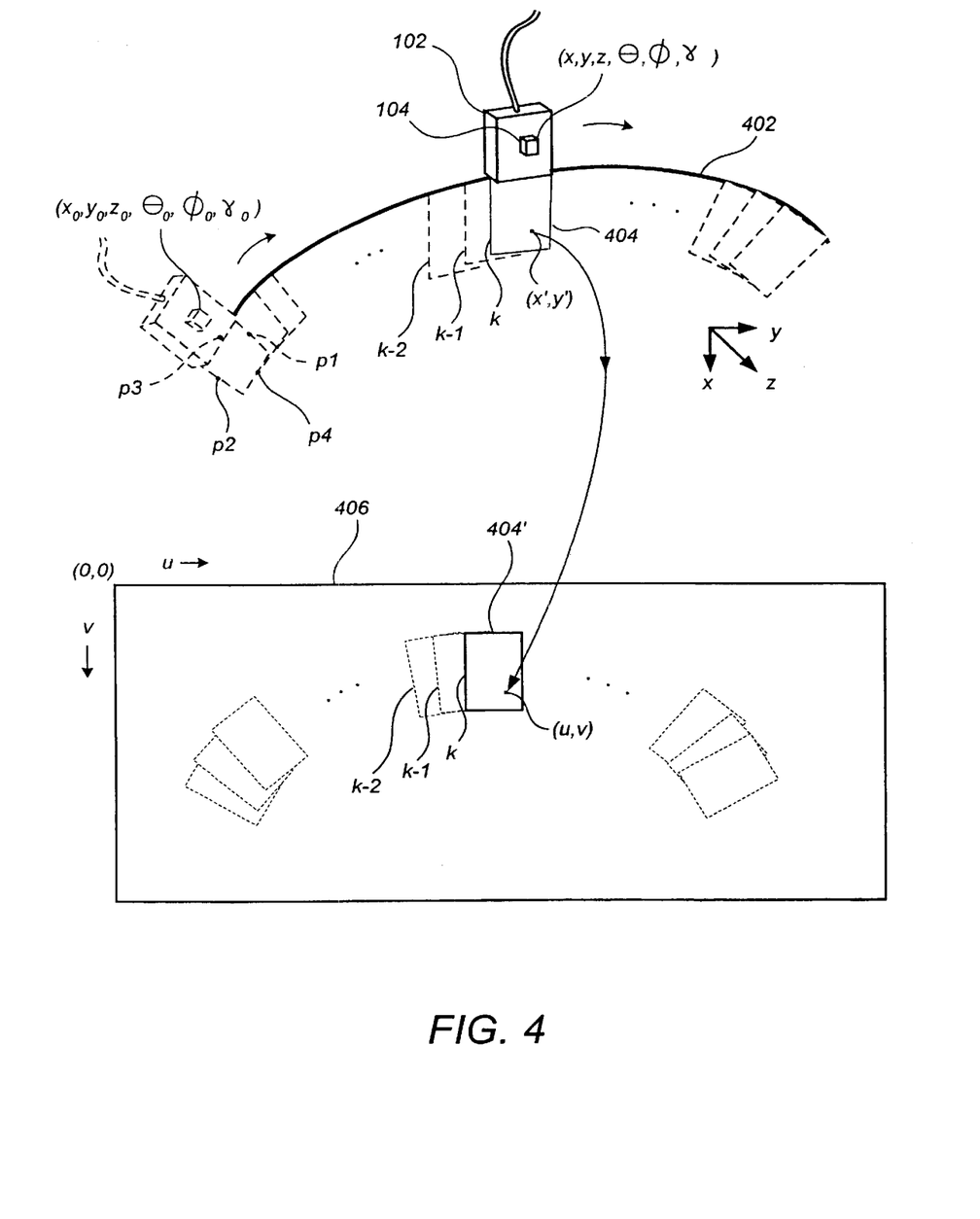
FIG. 4 shows a conceptual diagram of ultrasound scan frames being mapped into an output array in accordance with a preferred embodiment.

FIG. 4 shows a conceptual diagram of ultrasound frames being mapped into an output array in accordance with a preferred embodiment. In particular, FIG. 4 shows ultrasound transducer 102 moving across a target surface 402 at a point in time when the $k^{th}$ scan frame 404 is being generated, this scan frame being denoted herein by the array f(k,x',y'), where x' and y' are coordinates measured with respect to ultrasound transducer 102. In dotted lines, FIG. 4 also shows the ultrasound transducer 102 in its initial position, as well as four reference points p1, p2, p3, and p4 whose coordinates $(x_{p1}, y_{p1}, z_{p1})$, $(x_{p2}, y_{p2}, z_{p2})$, $(x_{p3}, y_{p3}, z_{p3})$, and $(x_{p4}, y_{p4}, z_{p4})$, respectively, are subsequently used in the algorithm. Using the known values for the detected transducer coordinates $(x, y, z, \theta, \phi, \gamma)$ for the $k^{th}$ scan frame, as well as all the coordinate information known for the initial scan frame, the relative coordinates (x',y') for each location in scan frame 404 are mapped to new coordinates (u,v) in an output array 406, landing in a similarly-shaped portion 404' as shown in FIG. 4. In particular, the new coordinates (u,v) (as well as a departure metric w to be described infra with respect to FIG. 7) may be computed according to the equations listed in Appendix A. In viewing those equations, it is helpful to note that (i) x' and y' are the input values that vary with each location in a scan frame, (ii) x, y, z, $\theta$, $\phi$, and $\gamma$ are the input values that vary with transducer position, and (iii) the output values are u, v, and w. All other variables are either intermediate variables or initial coordinate values that remain fixed as the transducer 102 is swept across the target.

Figure 5:
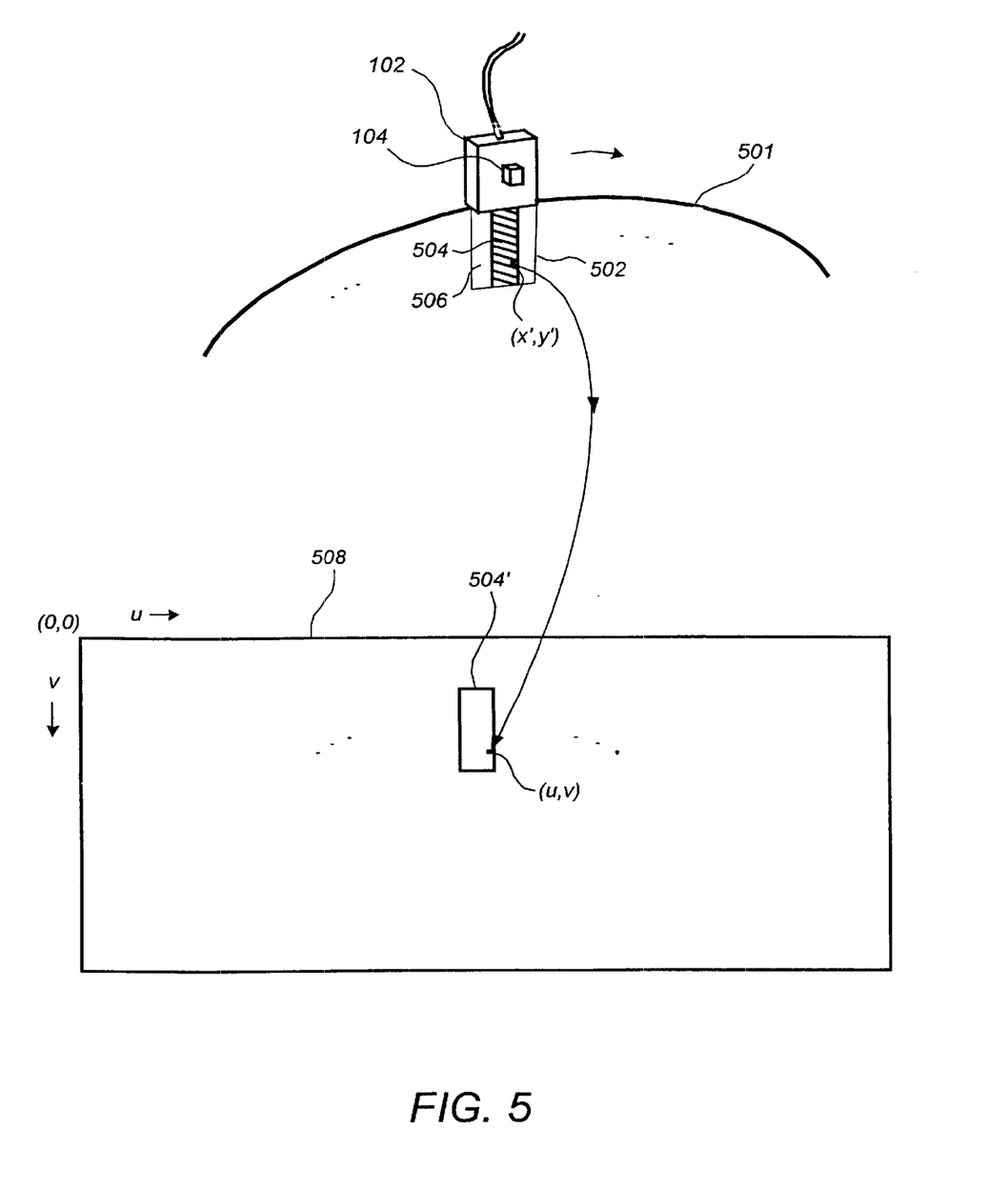
FIG. 5 shows a conceptual diagram of the use of selective portions of a scan frame area in generating scan frames in accordance with a preferred embodiment.

FIG. 5 shows a conceptual diagram of the use of selective portions of a scan frame area in generating scan frames in accordance with a preferred embodiment. FIG. 5 shows a configuration similar to FIG. 4, with ultrasound transducer 102 being swept across a target surface 501 and detecting acoustic reflectivity data for a scan frame area 502. In accordance with a preferred embodiment, only scan lines near the center of scan frame area 502 are used to generate the scan frames f(k,x',y') for mapping into the output array. Thus, only the area 504 is included in the scan frame data f(k,x',y') and mapped into a corresponding area 504' in the output array. The remainder of the readings, shown as area 506 in FIG. 5, are discarded. It has been found that under most conditions there is an adequate number of scan frame readings compounded for a given output array location even when a substantial portion of the scan frame readings are discarded. For example, as described supra, approximately 400 scan frame readings are compounded for each output array location in a system having a 5 cm-long transducer moving at 5 cm/s over a target with a frame rate of 20 fps. Accordingly, because scan lines near the center of a scan frame area have more precise readings than scan lines farther away from the center, a substantial portion of outer scan line readings may be discarded. In one preferred embodiment, only the center 50 percent of the scan line readings are used, and the remainder are discarded.

Figure 6:
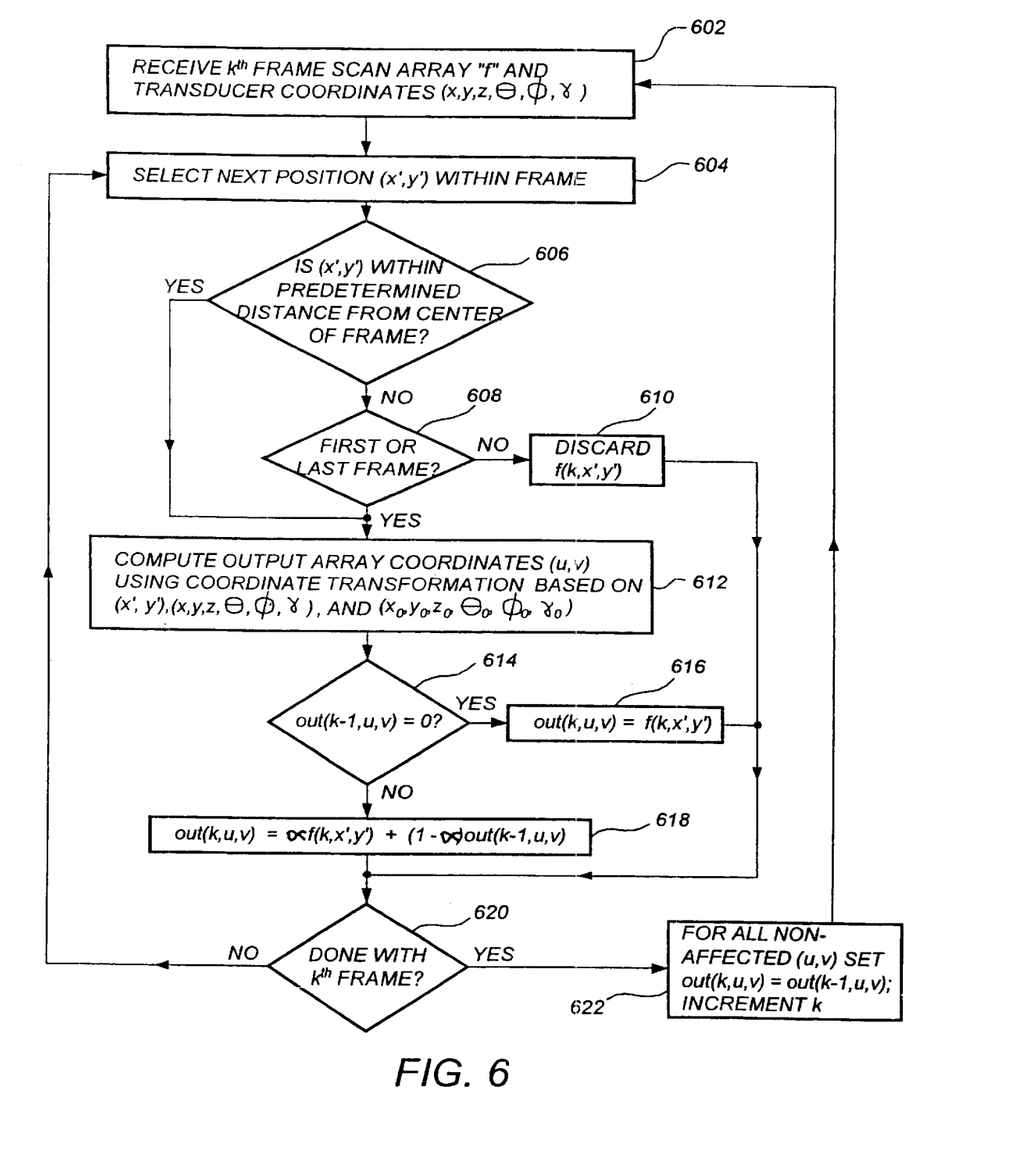
FIG. 6 shows steps for computing an extended view ultrasound image from scan frames and position parameters in accordance with a preferred embodiment.

FIG. 6 shows steps for computing an extended view ultrasound image from scan frames and position parameters in accordance with a preferred embodiment, these steps generally being performed by ultrasound processing unit 108 and corresponding to step 312 of FIG. 3. At step 602, the $k^{th}$ scan frame array f(k,x',y') and transducer coordinates (x, y, z, θ, φ, γ) are received. For each scan frame f(k,x',y'), at step 604 a next position (x',y') is selected. At step 606, it is determined whether the location (x',y') corresponds to a scan line within a predetermined distance from the center of the scan frame area, as described supra with respect to FIG. 5. If so, the algorithm continues at step 612. If not, then at steps 608 and 610 that data point is discarded unless that scan frame is the very first frame or the very last frame taken in the extended view scan. If the scan frame is the very first frame or the very last frame, it is necessary to fill out the data to the end of the target region, and so readings from these outer scan lines are not discarded. Otherwise, where the scan frame is not the very first frame or the very last frame and the location (x',y') corresponds to a scan line outside the predetermined distance from the center of the scan frame area, transducer array, the data is discarded at step 610 and the algorithm continues at step 620.

At step 612, the relative coordinates (x',y') are mapped to new coordinates (u,v) using the known values for the detected transducer coordinates (x, y, z, θ, φ, γ) versus the initial transducer coordinates $(x_0, y_0, z_0, \theta_0, \phi_0, \gamma_0)$, in accordance with the equations listed in Appendix A, as referenced supra. At step 614, for the point (u,v) in the output array, it is determined whether the previous output array value out(k−1,u,v) is equal to 0 or, more generally, to a null initialized value. If so, then there is no previous value to blend with the current scan frame value, and therefore at step 616 the current output array value out(k,u,v) is set equal to the current scan frame value f(k,x',y'), and then the algorithm continues at step 620. If there is a previous value to blend, then at step 618 the current output array value out(k,u,v) is set equal to the sum of the current scan frame value f(k,x',y') weighted by a weighting value a and the previous output array value out(k−1,u,v) weighted by (1−α), and the algorithm continues at step 620. The algorithm performed by steps 614–618 is summarized below in Eq. (1):

$$\text{out}(k, u, v) = \begin{cases} f(k, x', y') & \text{if out}(k-1, u, v) = NULL \\ \alpha f(k, x', y') + (1-\alpha)\text{out}(k-1, u, v) & \text{otherwise} \end{cases} \quad \{1\}$$

At step 620, it is determined whether the location (x',y') was the final location of scan frame f(x',y'). If not, the algorithm for the $k^{th}$ scan frame continues at step 604. If so, then the previous output array values out(k−1,u,v) for all locations (u,v) in the output array that were not affected during the processing of the $k^{th}$ scan frame are carried forward and assigned as the current output array values out(k,u,v) at step 622. Also at step 622, the frame counter variable k is incremented and the next scan frame is received at step 602.

It has been found that the above alpha blending algorithm, when applied to successive scan frames in accordance with the preferred embodiments, produces a stable, high-quality extended view output image with decreased speckle, increased signal-to-noise ratio, and enhanced contrast resolution. In one preferred embodiment, the value for α is a fixed predetermined value that may be optimally chosen based on the specific parameters of a given implementation. Although the lower and upper limits for α are 0.0 and 1.0, respectively, it has been found that values for α in the range of 0.4 to 0.9 yield particularly good results. Generally speaking, α may be set closer to 1.0 for increased temporal resolution, such as for capturing the positional extremities of a beating heart, while it may be set farther from 1.0 (i.e., closer to 0.0) for decreased speckle and increased signal-to-noise performance, such as for imaging stationary tissue. Accordingly, in a preferred embodiment, the value for α is a user adjustable quantity that may be adjusted using any of a variety of input mechanisms such as a knob near the display device 110 or a keyboard input. Where the frames overlap spatially to such an extent that the value of a point (pixel) in the extended view image typically would result from combining the values of spatially matched points of several frames, the weighting factors α and (1−α) can be applied to information from a current frame and the combination of information from two or more previous frames. Stated differently, these factors are first applied to information from two successive frames, then to the result and information from a third frame, etc., until a new frame is so far away spatially that it should no longer contribute information to the relevant point of the extended view image.

In additional preferred embodiments, the weighting factor α can be automatically and dynamically adjusted on a per pixel or per segment basis responsive to various imaging factors. Since it is known, for example, that locations of low acoustic reflectivity benefit more from image compounding that locations of high acoustic reflectivity, the value of α can be dynamically adjusted lower for locations experiencing low acoustic reflectivity for reducing speckle, and can be dynamically adjusted higher for locations experiencing high acoustic reflectivity for increasing temporal contrast. In another preferred embodiment, since moving edges are better discerned in a high temporal contrast system, edge motion detection algorithms can be incorporated, wherein locations corresponding to high tissue motion will have a higher α while locations corresponding to stationary tissue will have a lower α. In still another preferred embodiment, since tissue generally moves faster during a systolic cycle than a diastolic cycle, α can be adjusted to a higher value during a systolic cycle and adjusted to a lower value during a diastolic cycle.

Figure 7:
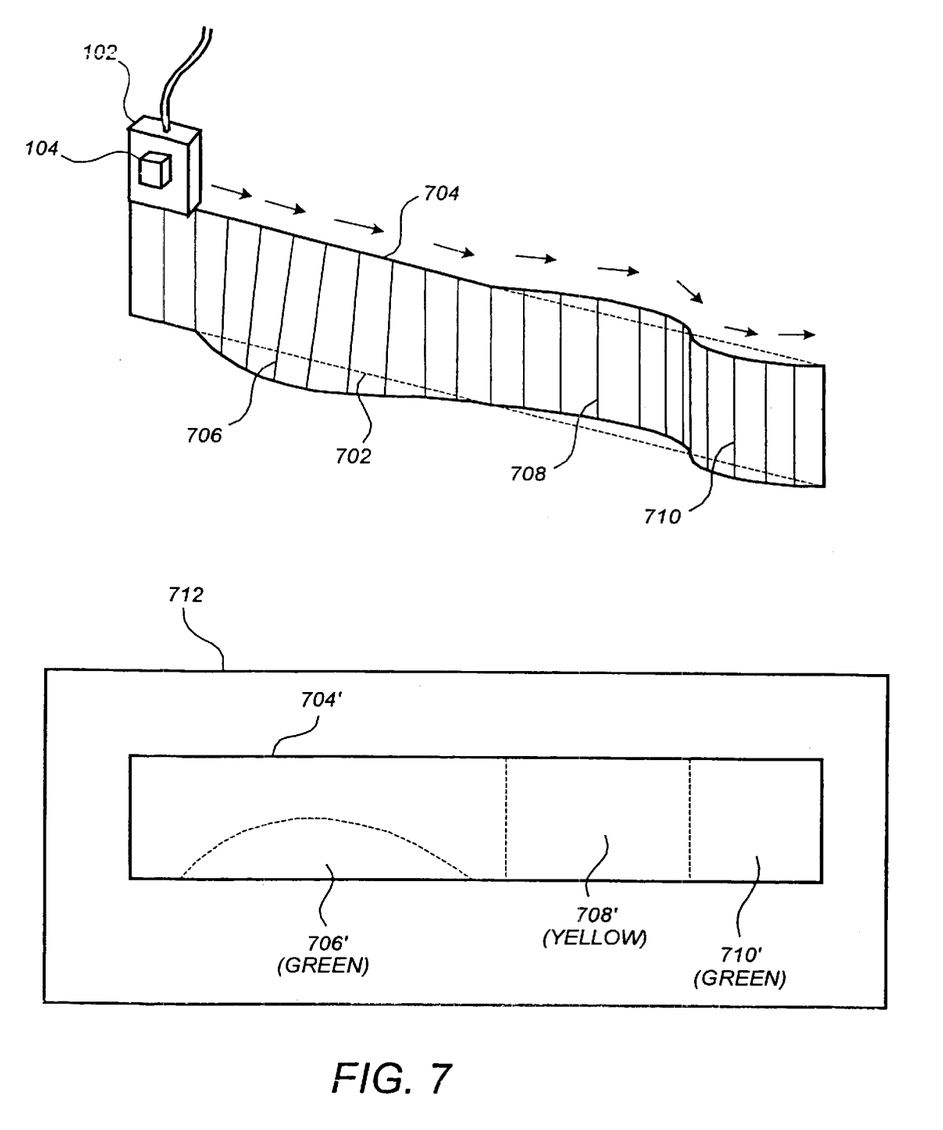
FIG. 7 shows a conceptual diagram of a ribbon-like path traversed by a transducer and a corresponding augmented extended view ultrasound output display in accordance with a preferred embodiment.

FIG. 7 shows a conceptual diagram of a ribbon-like path traversed by a transducer and a corresponding augmented output display in accordance with a preferred embodiment. In contrast to prior art systems that require the transducer to remain in a substantially common plane during the extended view scan, a system in accordance with the preferred embodiments is highly robust against transducer departures from the common plane. In accordance with a preferred embodiment, in addition to remaining stable during these transducer departures, the amount of departure from a common plane is measured and displayed to the user for assistance in interpreting the extended view ultrasound image.

Shown in FIG. 7 is a ribbon-like path 704 traversed by ultrasound transducer 102 across the surface of the target. A reference plane or intended plane 702 is shown in dotted lines, and will generally correspond to path that the user initially embarked on. Alternatively, the reference plan 702 can be established after the scan is complete using a minimum squared error approach or the like. In the transducer trajectory shown in FIG. 7, after a short distance the user tilted the transducer to create a flared out path portion 706 and then subsequently moved the transducer in an "S" shaped direction shown near locations 708 and 710. According to a preferred embodiment, a departure metric is calculated for each locations along the ribbon-like path. For example, a simple linear distance between a point on the ribbon-like path 704 and the reference plane 702 is represented by the variable "w" in Eq. (2) of Appendix A, where the initial transducer coordinates ($x_0$, $y_0$, $z_0$, $\theta_0$, $\phi_0$, $\gamma_0$) are used to establish the location of the reference plane 702. Other metrics, such as an angular metric between the angle of the transducer 102 and the reference plane 702, may alternatively be used.

FIG. 7 further shows an output array 712 comprising an extended view image 704'. Superimposed on extended view image 704' in areas 706', 708', and 710' are indications of the amount of departure from the reference plane 702 at each location. For example, if the extended view image 704' is normally a black and white display, tissue locations in area 706' may be colored green to represent departure in a first direction, with the amount of green tinting representing the magnitude of the linear departure metric w. Tissue locations in area 708' may be colored yellow to represent departure in a second direction, with the amount of yellow tinting likewise representing the magnitude of the linear departure metric w. Alternatively, a separate graph lying above the extended view image 704 may be presented, comprising a single-line plot of a composite departure metric for each scan line in the extended view image. A variety of other representations of departure metrics superimposed upon the extended view ultrasound image are within the scope of the preferred embodiments.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, a system in accordance with the preferred embodiments may be used with color Doppler systems, power Doppler systems, and other systems. For color output displays, an alpha-blending algorithm may be separately applied to each component color plane, with different alpha-blending weights used for each component color plane. Therefore, reference to the details of the preferred embodiments are not intended to limit their scope, which is limited only by the scope of the claims set forth below.

APPENDIX A

COORDINATE TRANSFORMATION EQUATIONS

In viewing these equations, it is helpful to note the following: (i) x' and y' are the input values that vary with each location in a scan frame and appear in Eq. (1), (ii) x, y, z, $\theta$, $\phi$, and $\gamma$ are the input values that vary with transducer position, and (iii) the output values are u, v, and w and appear in Eq. (2). All other variables are either intermediate variables or initial coordinate values that remain fixed for a given extended view scanning sequence.

$$\begin{bmatrix} u' \\ v' \\ w' \end{bmatrix} = \begin{bmatrix} x - x_0 \\ y - y_0 \\ z - z_0 \end{bmatrix} + \begin{bmatrix} x' \\ y' \\ 0 \end{bmatrix} \begin{bmatrix} T11 & T12 & T13 \\ T21 & T22 & T23 \\ T31 & T32 & T33 \end{bmatrix} \quad \{1\}$$

$$\begin{bmatrix} u \\ v \\ w \end{bmatrix} = \begin{bmatrix} u' \\ v' \\ w' \end{bmatrix} \begin{bmatrix} R11 & R12 & R13 \\ R21 & R22 & R23 \\ R31 & R32 & R33 \end{bmatrix} \quad \{2\}$$

$$\begin{bmatrix} x_x \\ x_y \\ x_z \end{bmatrix} = \begin{bmatrix} x_{p2} \\ y_{p2} \\ z_{p2} \end{bmatrix} - \begin{bmatrix} x_{p1} \\ y_{p1} \\ z_{p1} \end{bmatrix} \quad \{3\}$$

$$\begin{bmatrix} y_x \\ y_y \\ y_z \end{bmatrix} = \begin{bmatrix} x_{p4} \\ y_{p4} \\ z_{p4} \end{bmatrix} - \begin{bmatrix} x_{p3} \\ y_{p3} \\ z_{p3} \end{bmatrix} \quad \{4\}$$

$$d1 = \sqrt{\left[y_y\left(\frac{x_x y_z - x_z y_x}{x_x y_y - x_y y_x}\right) - y_z\right]^2 + \left[\left(\frac{x_x y_z - x_z y_x}{x_x y_y - x_y y_x}\right)^2 + 1\right]} \quad \{5\}$$

$$\begin{bmatrix} z_x \\ z_y \\ z_z \end{bmatrix} = \left(\frac{1}{d1}\right) \begin{bmatrix} y_y\left(\frac{x_x y_z - x_z y_x}{x_x y_y - x_y y_x}\right) - y_z \\ -y_x\left(\frac{x_x y_z - x_z y_x}{x_x y_y - x_y y_x}\right) \\ y_x\left(\frac{x_x y_z - x_z y_x}{x_x y_y - x_y y_x}\right) - y_z \end{bmatrix} \quad \{6\}$$

$$\begin{bmatrix} xn_x \\ xn_y \\ xn_z \end{bmatrix} = \frac{1}{\sqrt{x_x^2 + x_y^2 + x_z^2}} \begin{bmatrix} x_x \\ x_y \\ x_z \end{bmatrix} \quad \{7\}$$

$$\begin{bmatrix} yn_x \\ yn_y \\ yn_z \end{bmatrix} = \frac{1}{\sqrt{y_x^2 + y_y^2 + y_z^2}} \begin{bmatrix} y_x \\ y_y \\ y_z \end{bmatrix} \quad \{8\}$$

$$\begin{bmatrix} zn_x \\ zn_y \\ zn_z \end{bmatrix} = \frac{1}{\sqrt{z_x^2 + z_y^2 + z_z^2}} \begin{bmatrix} z_x \\ z_y \\ z_z \end{bmatrix} \quad \{9\}$$

$$R11 = \frac{xn_z(zn_y xn_z - xn_y zn_z)}{(yn_x xn_z - xn_x yn_z)(zn_y xn_z - xn_y zn_z) - (zn_x xn_z - xn_x zn_z)(yn_y xn_z - xn_y yn_z)} \quad \{10\}$$

$$R21 = \frac{-R11(zn_x xn_z - xn_x zn_z)}{(zn_y xn_z - xn_y zn_z)} \quad \{11\}$$

$$R31 = \frac{-(zn_x R11 - zn_y R21)}{zn_z} \quad \{12\}$$

$$R12 = \frac{-yn_z(xn_y yn_z - yn_y xn_z)}{(xn_x yn_z - yn_x xn_z)(zn_y yn_z - yn_y zn_z) - (zn_x yn_z - yn_x zn_z)(xn_y yn_z - yn_y xn_z)} \quad \{13\}$$

$$R22 = \frac{-R12(xn_x yn_z - yn_x xn_z)}{(xn_y yn_z - yn_y xn_z)} \quad \{14\}$$

$$R32 = \frac{-(yn_x R12 - yn_y R22)}{yn_z} \quad \{15\}$$

$$R13 = \frac{yn_z(zn_y yn_z - yn_y zn_z)}{(xn_x yn_z - yn_x xn_z)(zn_y yn_z - yn_y zn_z) - (zn_x yn_z - zn_y yn_x)(xn_y yn_z - yn_y xn_z)} \quad \{16\}$$

$$R23 = \frac{-R13(zn_x yn_z - yn_x zn_z)}{(zn_y yn_z - yn_y zn_z)} \quad \{17\}$$

$$R33 = \frac{-(yn_x R13 - yn_y R23)}{yn_z} \quad \{18\}$$

T11=cos $\phi$ cos $\theta$ \quad \{19\}

T21=−cos $\gamma$ sin $\theta$+sin $\gamma$ sin $\phi$ cos $\theta$ \quad \{20\}

$T31 = \sin\gamma \sin\theta + \cos\gamma \sin\phi \cos\theta$ {21}

$T12 = \cos\phi \sin\theta$ {22}

$T22 = \cos\gamma \cos\theta + \sin\gamma \sin\phi \sin\theta$ {23}

APPENDIX A

COORDINATE TRANSFORMATION
EQUATIONS (CONT.)

$T32 = -\sin\gamma \cos\theta + \cos\gamma \sin\phi \sin\theta$ {24}

$T13 = -\sin\theta$ {25}

$T23 = \sin\gamma \cos\phi$ {26}

$T33 = \cos\gamma \cos\phi$ {27}

What is claimed is:

1. A method for generating an extended view ultrasound image, comprising the steps of:

generating a plurality of scan frames as a transducer is moved across a target;

detecting transducer position information corresponding to each of said scan frames, said position information including location and orientation information; and using said transducer position information to form an extended view image from said scan frames;

initializing an output array; and sequentially processing said scan frames and updating said output array as each scan frame is processed;

wherein said extended view image comprises at least a portion of said output array;

said scan frames being at least partially overlapping, wherein a blending algorithm is used at each overlapping location to update said output array based on a current scan frame value at that location and at least one previous scan frame value at that location;

said blending algorithm comprising the steps of:

weighting the current scan frame value at that location by a first weighting factor to produce a first intermediate result;

weighting the previous output array value at that location by a second weighting factor to produce a second intermediate result; and setting the current value of the output array at that location to a sum of said first and second intermediate results;

wherein said first weighting factor is equal to a value $\alpha$, and wherein said second weighting factor is equal to $(1-\alpha)$; and wherein $\alpha$ is a predetermined fixed value greater than or equal to 0.4 and less than or equal to 0.9.

2. A method for generating an extended view ultrasound image, comprising the steps of:

generating a plurality of scan frames as a transducer is moved across a target;

detecting transducer position information corresponding to each of said scan frames, said position information including location and orientation information; and using said transducer position information to form an extended view image from said scan frames;

initializing an output array; and sequentially processing said scan frames and updating said output array as each scan frame is processed;

wherein said extended view image comprises at least a portion of said output array;

said scan frames being at least partially overlapping, wherein a blending algorithm is used at each overlapping location to update said output array based on a current scan frame value at that location and at least one previous scan frame value at that location;

said blending algorithm comprising the steps of:

weighting the current scan frame value at that location by a first weighting factor to produce a first intermediate result;

weighting the previous output array value at that location by a second weighting factor to produce a second intermediate result; and setting the current value of the output array at that location to a sum of said first and second intermediate results;

wherein said first weighting factor is equal to a value $\alpha$, and wherein said second weighting factor is equal to $(1-\alpha)$; and wherein $\alpha$ is a user-adjustable value, whereby $\alpha$ may be set closer to 1.0 than to 0.0 for increased temporal resolution, and whereby $\alpha$ may be set closer to 0.0 than to 1.0 for decreased speckle and increased signal to noise performance.

3. A method for generating an extended view ultrasound image, comprising the steps of:

generating a plurality of scan frames as a transducer is moved across a target;

detecting transducer position information corresponding to each of said scan frames, said position information including location and orientation information; and using said transducer position information to form an extended view image from said scan frames;

initializing an output array; and sequentially processing said scan frames and updating said output array as each scan frame is processed;

wherein said extended view image comprises at least a portion of said output array;

said scan frames being at least partially overlapping, wherein a blending algorithm is used at each overlapping location to update said output array based on a current scan frame value at that location and at least one previous scan frame value at that location;

said blending algorithm comprising the steps of:

weighting the current scan frame value at that location by a first weighting factor to produce a first intermediate result;

weighting the previous output array value at that location by a second weighting factor to produce a second intermediate result; and setting the current value of the output array at that location to a sum of said first and second intermediate results;

wherein said first weighting factor is equal to a value $\alpha$, and wherein said second weighting factor is equal to $(1-\alpha)$; and wherein $\alpha$ is automatically and dynamically adjusted on a per location basis, wherein $\alpha$ is increased for locations of high ultrasound reflectivity, and wherein $\alpha$ is decreased for locations of low ultrasound reflectivity.

4. A method for generating an extended view ultrasound image, comprising the steps of:

generating a plurality of scan frames as a transducer is moved across a target;

detecting transducer position information corresponding to each of said scan frames, said position information including location and orientation information; and using said transducer position information to form an extended view image from said scan frames;

initializing an output array; and sequentially processing said scan frames and updating said output array as each scan frame is processed;

wherein said extended view image comprises at least a portion of said output array;

said step of sequentially processing and updating comprising the steps of:
  mapping each location in the current scan frame to a corresponding location of said output array;
  if the previous output array value at that location is equal to its initialized value, setting the current value of the output array at that location to the current scan frame value;
  if the previous output array value at that location is not equal to its initialized value, performing the steps of:
    weighting the current scan frame value at that location by a first weighting factor to produce a first intermediate result;
    weighting the previous output array value at that location by a second weighting factor to produce a second intermediate result; and
    setting the current value of the output array at that location to a sum of said first and second intermediate results.

5. The method of claim 4, wherein said first weighting factor is equal to a value α, and wherein said second weighting factor is equal to (1−α).

6. The method of claim 5, said transducer comprising a linear array of elements used in defining a scan frame area, said scan frame area comprising a plurality of scan lines, wherein said scan frames are generated only from scan lines that are within a predetermined distance of a center line of said scan frame area.

7. The method of claim 6, wherein said predetermined distance is less than 25% of a width of the scan frame area.

8. The method of claim 5, wherein said scan frames are of a type selected from a group consisting of: B-mode, color Doppler mode, and power Doppler mode.

9. A method for generating an extended view ultrasound image, comprising the steps of:
  generating a plurality of scan frames as a transducer is moved across a target;
  detecting transducer position information corresponding to each of said scan frames, said position information including location and orientation information; and
  using said transducer position information to form an extended view image from said scan frames;
  initializing an output array; and
  sequentially processing said scan frames and updating said output array as each scan frame is processed;
  wherein said extended view image comprises at least a portion of said output array;
  said scan frames being at least partially overlapping, wherein a blending algorithm is used at each overlapping location to update said output array based on a current scan frame value at that location and at least one previous scan frame value at that location:
  establishing an intended target plane based on at least one transducer position as the transducer is moved across the target;
  for each scan frame, using its corresponding transducer position information to compute a departure metric between said intended target plane and the plane of the scan frame and; and
  for each scan frame, superimposing information related to said departure metric onto corresponding locations of said extended view image;
  wherein said step of superimposing information comprises the steps of:
    determining, for a plurality of locations in each scan frame, a linear distance between said location and said intended target plane; and
    coloring the corresponding location in said extended view image with a color representative of said linear distance;
  wherein said step of superimposing information comprises the step of displaying a separate trace near said extended view image that communicates a magnitude of said departure metric for corresponding groups of extended view image locations.

10. An extended view ultrasound imaging system, comprising:
  an ultrasound transducer, said ultrasound transducer being capable of generating scan frames while being swept across a target surface, said scan frames defining a ribbon-like path through the target as the ultrasound transducer is swept across the target surface;
  a sensor for detecting ultrasound transducer position information corresponding to each scan frame, said position information including location and orientation information;
  a processor for receiving the scan frames and corresponding position information and generating therefrom an output array comprising acoustic reflectivity data for each location along said ribbon-like path; and
  an output device for displaying said output array to a user;
  said processor being adapted to perform the steps of:
    initializing the output array to null values;
    mapping each location in a current scan frame to a corresponding location of the output array; and
    updating the output array based on a previous value of the output array at that location and the value of the current scan frame at that location.

11. The system of claim 10, said processor being further adapted to perform the steps of:
  establishing a reference plane based on at least one ultrasound transducer position as said ultrasound transducer is moved across the target;
  using the ultrasound transducer position information associated with each scan frame to determine a departure amount between the ribbon-like path and the reference plane for each location in the scan frame;
  converting said departure amount into a user perceivable representation for transfer to said output device.

12. The system of claim 11, said departure amount comprising a linear distance between the ribbon-like path and the reference plane for each location in the scan frame.

13. The system of claim 12, said departure amount comprising an angular distance between a plane of the ultrasound transducer and said reference plane for each location in the scan frame.

14. The system of claim 13, said step of converting said departure amount into a user perceivable representation comprising the step of creating a pixel color representative of said linear distance.

15. The system of claim 10, wherein for each location in the current scan frame said processor is further adapted to perform the steps of:
   if the previous output array value is equal to a null value, setting the current value of the output array equal to the current scan frame value;
   if the previous output array value is not equal to a null value, performing the steps of:
      weighting the current scan frame value by a first weighting factor to produce a first intermediate result;
      weighting the previous output array value by a second weighting factor to produce a second intermediate result; and
      setting the current value of the output array to a sum of said first and second intermediate results.

16. The system of claim 15, wherein said first weighting factor is equal to a value $\alpha$, and where in said second weighting factor is equal to $(1-\alpha)$.

17. The system of claim 16, said ultrasound transducer comprising a linear array of elements used in defining a scan frame area, said scan frame area comprising a plurality of scan lines, wherein said scan frames are generated only from scan lines that are within a predetermined distance of a center line of said scan frame area.

18. The method of claim 17, wherein said predetermined distance is less than 25% of a width of the scan frame area.

19. The system of claim 17, wherein $\alpha$ is a predetermined fixed value greater than or equal to 0.4 and less than or equal to 0.9.

20. The system of claim 17, wherein $\alpha$ is a user-adjustable value, whereby $\alpha$ may be set closer to 1.0 than to 0.0 for increased temporal resolution, and whereby a may be set closer to 0.0 than to 1.0 for decreased speckle and increased signal to noise performance.

21. The system of claim 17, wherein $\alpha$ is automatically and dynamically adjusted on a per location basis, wherein $\alpha$ is increased for locations of high ultrasound reflectivity, and wherein $\alpha$ is decreased for locations of low ultrasound reflectivity.

22. The system of claim 17, wherein said processor is adapted to detect tissue motion in the target using information from the successive scan frames, wherein $\alpha$ is automatically and dynamically adjusted on a per location or per segment basis, wherein $\alpha$ is increased for locations of faster tissue movement for increased temporal resolution, and wherein $\alpha$ is decreased for locations of slower tissue movement for decreased speckle and increased signal to noise performance.

23. The system of claim 17, wherein said processor is adapted to receive, for each scan frame, information relating that scan frame to a systolic or diastolic cycle, wherein $\alpha$ is automatically and dynamically adjusted on a per scan frame basis, wherein $\alpha$ is increased for scan frames during the systolic cycle for increased temporal resolution, and wherein $\alpha$ is decreased for scan frames during the diastolic cycle for decreased speckle and increased signal to noise performance.

* * * * *